United States Patent [19]

Oshiyama

[11] Patent Number: 4,976,708
[45] Date of Patent: Dec. 11, 1990

[54] BLOOD RESERVOIR

[75] Inventor: Hiroaki Oshiyama, Fuji, Japan

[73] Assignee: Terumo Kabushiki Kaisha, Tokyo, Japan

[21] Appl. No.: 366,731

[22] Filed: Jun. 15, 1989

[30] Foreign Application Priority Data

Jun. 21, 1988 [JP] Japan .................................. 63-153020
Dec. 9, 1988 [JP] Japan .................................. 63-311590

[51] Int. Cl.$^5$ ............................................. A61B 19/00
[52] U.S. Cl. ................................. 604/408; 604/410; 604/4; 604/122
[58] Field of Search ................... 604/4, 5, 6, 403, 406, 604/408, 410, 122, 317, 124, 126; 128/DIG. 3

[56] References Cited

U.S. PATENT DOCUMENTS

| 3,985,135 | 10/1976 | Carpenter et al. | 604/410 |
| 4,493,705 | 1/1985 | Gordon et al. | 604/122 |
| 4,622,032 | 11/1986 | Katsura et al. | 604/122 |
| 4,643,713 | 2/1987 | Viitala | 604/4 |
| 4,717,377 | 1/1988 | Fukasawa | 604/4 |
| 4,734,269 | 3/1988 | Clarke et al. | 604/122 X |

FOREIGN PATENT DOCUMENTS

| A1-0080610 | 6/1983 | European Pat. Off. . |
| 0183057 | 6/1986 | European Pat. Off. . |
| 0206638 | 12/1986 | European Pat. Off. . |
| 3328562 | 2/1984 | Fed. Rep. of Germany . |
| 58-99968 | 6/1983 | Japan . |
| 69-67962 | 4/1984 | Japan . |
| 59-131357 | 7/1984 | Japan . |
| 62-15349 | 1/1987 | Japan . |
| WO 86/02825 | 5/1986 | PCT Int'l Appl. . |

Primary Examiner—Robert A. Hafer
Assistant Examiner—Lynda M. Cofsky
Attorney, Agent, or Firm—Frishauf, Holtz, Goodman & Woodward

[57] ABSTRACT

In a blood reservoir comprising a container casing defining a space for accommodating blood, the casing having a generally rectangular contour defining a pair of top and bottom sides and a pair of laterally opposed sides, provided that the casing assumes a vertically upright attitude, an inlet port is disposed in one lateral side of the casing for introducing blood into the space, an outlet port is disposed in the bottom side of the casing for discharging blood from the space, and a vent port disposed in the top side of the casing in fluid communication with the space. In another form, a partition separates the space into upper and lower compartments, and apertures are formed in the partition for allowing partial fluid communication between the compartments. The inlet port and the vent port are in communication with the upper compartment, and the outlet port is in communication with the lower compartment.

22 Claims, 11 Drawing Sheets

BLOOD RESERVOIR

This invention relates to an improvement in a blood reservoir for use in the medical field. The blood reservoir is inserted in an extracorporeal circuit, typically an artificial heart-lung circuit for temporarily storing blood drained from the patient.

BACKGROUND OF THE INVENTION

An extracorporeal blood circuit often experiences variations in the flow rate of blood, for example, when the amount of blood drained from the patient decreases or when the amount of blood fed to the patient must be increased. An extra amount of blood should be stored in the circuit to accommodate such variations in blood flow rate. To this end, a blood reservoir is inserted in the circuit for temporarily storing venous blood drained from the patient. This type of reservoir is often called a venous reservoir.

One typical venous reservoir includes a pair of plastic sheets sealed along their four sides for defining a closed space therein. This closed type of venous reservoir has no risks of contact with air, entry of foreign matters, or pumping-in of air even when the amount of blood drained decreases.

The venous reservoir should preferably have the following functions.

(a) Blood storage function: The reservoir should have a sufficient volume or space to accommodate a necessary volume of blood.

(b) Debubbling function: Air bubbles can be introduced into a drainage tube when a blood drainage catheter is unsteadily dwelled in the vein or when the catheter is withdrawn from the vein. It is required to remove air from the drained blood in the reservoir.

(c) No stagnation: The reservoir should be free of local stagnation of blood.

Requirement (b), debubbling or air removal is a critical factor. If the reservoir does not function well in air removal, there is a possibility that air be introduced into the patient, causing thrombi in blood capillaries of various organs of the patient, particularly of the brain, eventually inviting cerebropathy after the operation and leaving a life threatening crisis.

In general, debubbling ability is improved as the blood storage volume of the reservoir increases. However, it is not recommendable to increase the blood storage volume. An increased blood storage volume increases the priming quantity of an overall extracorporeal circuit and requires a correspondingly increased amount of blood transfused, which increases the possible occurrence of hepatitis after the operation. An increased blood storage volume is also undesirable from the standpoint of blood saving.

For this reason, efforts have been made to develop a blood reservoir capable of efficient removal of air bubbles without increasing the blood storage volume.

One such attempt is the venous reservoir disclosed in Japanese Patent Application Kokai No. 67962/1984. Referring to FIG. 15, there is illustrated a venous reservoir at 100 as comprising a flexible container casing 101 defining a blood storage space 102 therein. The casing 101 is formed by sealing a pair of plastic sheets along their four sides. A blood inlet port in the form of a tube 105 is attached to the lower portion of the casing 101 such that the distal end 105a of the tube protrudes into the space 102. The distal portion 105a of the inlet tube 105 is provided with a plurality of apertures 106 so that drainage blood may be introduced into the space 102 through the inlet tube 105 in a dispersed manner. Then blood moderately flows into the space 102 from the inlet tube 105, contributing to maintenance of an environment where air bubbles will rise vertically upward through the blood under the impetus of buoyancy of bubbles themselves.

A blood outlet port in the form of a tube 107 is attached to the lower portion of the casing 101 at a predetermined spacing from the inlet port 105 and in parallel with the inlet port 105. A vent port 108 is disposed at the upper portion of the casing 101 in communication with the blood storage space 102. The casing 101 includes an extra sealed portion 101c defining a slant upper wall for the space 102 so that rising air bubbles may move along the slant upper wall 101c toward the vent port 108. Air bubbles escape outside the casing 101 through the vent port 108.

The venous reservoir 100 of the above-described construction has a likelihood of occurrence of a blood short-circuit that part of blood entering the space 102 from the apertures 106 in the inlet tube 105 directly flows toward the outlet port 107. Then some blood can be discharged or fed back to the extracorporeal circuit through the outlet port 107 without being fully debubbled. As a whole, this reservoir shows a less sufficient debubbling function.

The venous reservoir 100 of the prior art has an additional drawback that blood tends to locally stagnate in corners T near the bottom and the top of the space 102 surrounding the inlet tube 105 and the vent port 108, respectively.

There is a need for an improved blood reservoir which has overcome the above-mentioned problems.

SUMMARY OF THE INVENTION

A primary object of the present invention is to provide a new and improved blood reservoir having an efficient debubbling function and unsusceptible to local blood stagnation.

According to a first aspect of the present invention, there is provided a blood reservoir comprising a container casing defining a space for accommodating blood. The casing has a generally rectangular contour in a vertical plane defining a pair of upper and lower sides and a pair of laterally opposed sides, provided that the casing assumes a vertically upright attitude. An inlet port is disposed in at least one of the laterally opposed sides of the casing for introducing blood into the space, and an outlet port is disposed in the lower side of the casing for discharging blood from the space. A vent port is disposed in the upper side of the casing in fluid communication with the space.

In a typical example, the blood reservoir is incorporated in an artificial heart-lung circuit such that blood is drained from the patient into the reservoir before it is pumped to the oxygenator. The blood inlet port is disposed in one lateral side of the reservoir casing and the outlet port is disposed in the bottom side of the casing at a location remote from the inlet port. This arrangement of the inlet and outlet ports causes blood to travel a relatively long path from the inlet to the outlet. The blood inlet port is located relatively near to the vent port at the top, allowing air bubbles to travel a relatively short path to the vent port, ensuring more efficient debubbling.

Upon entry into the space through the inlet port, blood is distributed in multiple directions and thus forms a moderate flow, increasing the chance and time for entrained air bubbles to rise through the blood under the impetus of their own buoyancy. Since a blood stream is not so intense in the reservoir, little bubbles are positively entrained in the blood stream, ensuring spontaneous upward motion of bubbles.

Local stagnation of blood is minimized since the inlet port is disposed in the lateral side of the reservoir casing above the bottom.

According to a second aspect of the present invention, there is provided a blood reservoir comprising a container casing defining a space. The casing has a generally rectangular contour in a vertical plane defining a pair of upper and lower sides and a pair of laterally opposed sides, provided that the casing assumes a vertically upright attitude. Partition means separates the space into first and second compartments for accommodating blood, but allows partial fluid communication between the first and second compartments. An inlet port is in communication with the first compartment, and an outlet port is disposed in the lower side of the casing in communication with the second compartment. A vent port is disposed in the upper side of the casing in communication with the first compartment.

In the second form, the blood storage space of the reservoir is separated into two compartments which are in fluid communication through an opening. The flow of blood from the inlet port to the outlet port becomes more moderate, allowing more efficient rise of bubbles through the blood. More efficient debubbling is ensured.

More particularly, the blood which is drained from the patient along with air bubbles is first introduced into the first compartment of the reservoir through the inlet port. At this point, blood is distributed in multiple directions through a plurality of apertures formed in the inlet conduit, forming a moderate stream in the first compartment. Since the blood stream in the first compartment is not vigorous, air bubbles can readily rise by virtue of their buoyancy without being entrained on the stream. Upwardly collecting bubbles are then discharged to the exterior through the vent port.

Since blood is distributed in multiple directions in the first compartment, local stagnation of blood scarcely occurs in the first compartment.

The blood is introduced into the second compartment through the opening in the partition means after most bubbles have been removed. The second compartment serves for a secondary debubbling function by also allowing bubbles to rise through relatively calm blood. Upward collecting bubbles in the second compartment are discharged through an intermediate vent port formed in the partition means and then the top vent port.

BRIEF DESCRIPTION OF THE DRAWINGS

The above and other objects, features, and advantages of the present invention will be better understood from the following description taken in conjunction with the accompanying drawings, in which.

Throughout the figures, like parts are designated by he same numerals.

DESCRIPTION OF THE PREFERRED EMBODIMENTS

Several preferred embodiments of the blood reservoir of the present invention are illustrated with reference to the drawings.

Figure 14:
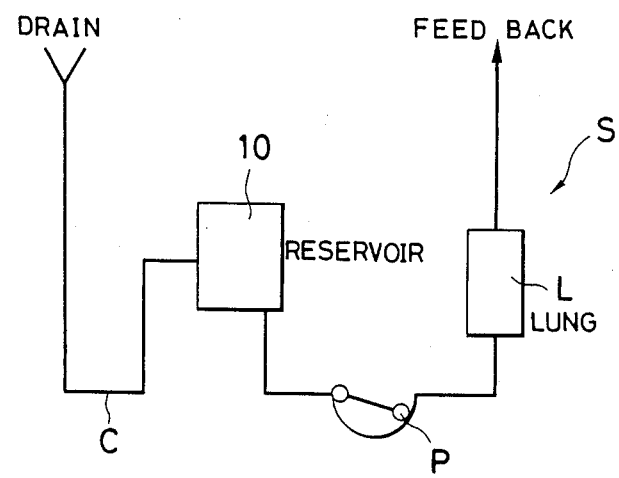
FIG. 14 diagrammatically illustrates an artificial heart-lung circuit to which the blood reservoir of the invention is applicable.

Before entering the description of embodiments, it will be helpful to briefly refer to an artificial heart-lung circuit to which the blood reservoir of the invention is applicable. FIG. 14 is a diagram showing such an artificial heart-lung circuit system S. The system includes an artificial lung or oxygenator L and a pump P in a circuit line C. Blood is drained from the patient (now shown) on the left side, pumped to lung L, and then fed back to the patient by passing along circuit line C. A blood reservoir designated at 10 is disposed in circuit line C upstream of pump P for the purpose of temporarily storing blood to accommodate any variations of blood flow rate through the system.

Figure 1:
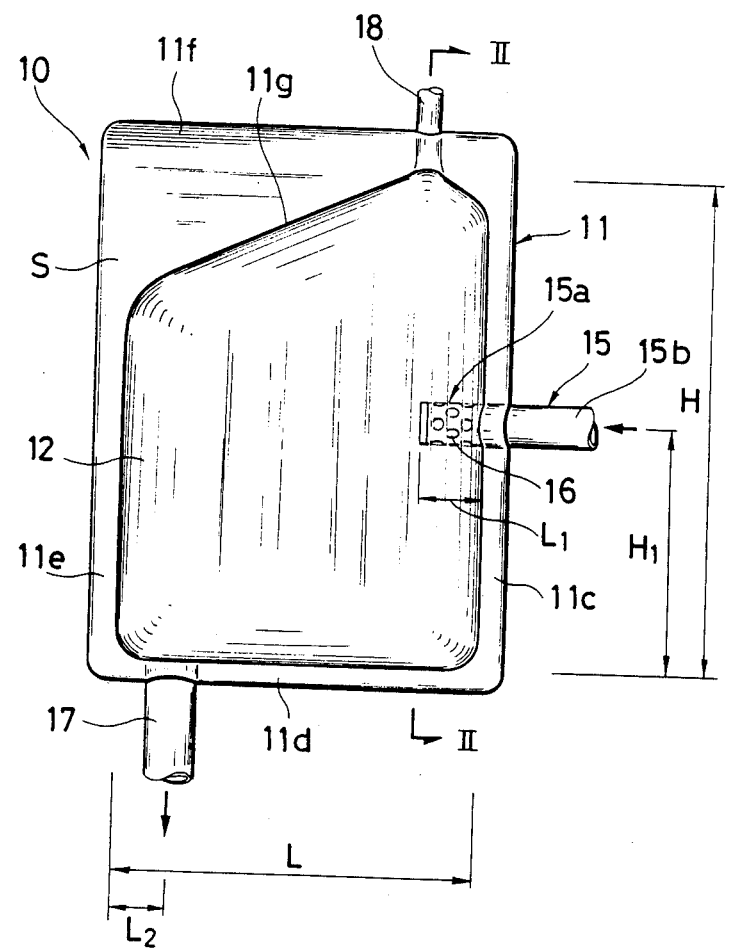
FIG. 1 is a front elevation of a blood reservoir according to a first embodiment of the invention.
Figure 2:
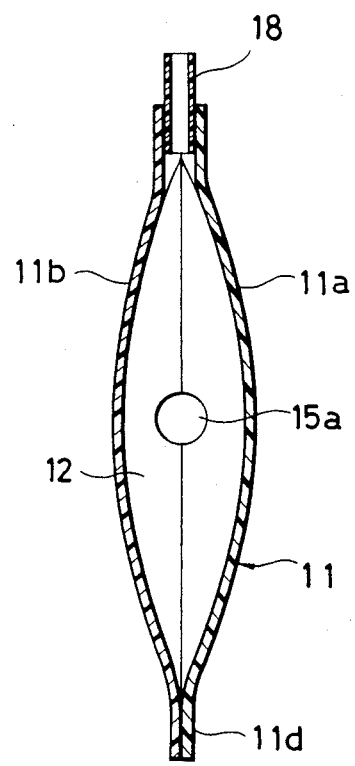
FIG. 2 is a cross section taken along lines II—II in FIG. 1.

FIG. 1 is a front elevation of a blood reservoir 10 according to a first embodiment of the invention. The blood reservoir normally assumes a vertical upright attitude as viewed in FIG. 1. FIG. 2 is a vertical cross section taken along lines II—II in FIG. 1.

The blood reservoir 10 includes a flexible container casing 11 defining a space 12 for storing blood therein. The blood storage space 12 has a predetermined volume. In the illustrated embodiment, the casing 11 is of the structure consisting essentially of a pair of generally rectangular plastic front and rear sheets 11a and 11b. The sheets may be of flexible vinyl chloride resin or similar flexible resin. They are placed in registry and joined together along the four sides as by heat sealing or RF welding. A seal S extends the entire perimeter of the sheets.

The casing 11 has a generally rectangular contour in a vertical plane (as viewed in FIG. 1) defining a pair of vertically opposed sides 11f and 11d and a pair of laterally opposed sides 11c and 11e. For the sake of brevity, the vertically opposed sides 11f and 11d are designated as top and bottom sides, and the laterally opposed sides 11c and 11e are designated as right and left sides, respectively.

A blood inlet port in the form of a conduit 15 is disposed in the right side 11c of casing 11, preferably at approximately a midpoint thereof, for introducing blood drained from the patient into the space 12. The inlet conduit 15 is integrally sealed between sheets 11a and 11b (see FIG. 2).

The inlet conduit 15 extends laterally into the space 12 and has a closed distal end 15a. The inlet conduit 15 may be a plastic tube having an inner diameter of 12.5 mm and an outer diameter of 17 mm, for example. An outer end 15b of inlet conduit 15 is adapted to be connected to the circuit line C of the artificial heart-lung system S diagrammatically shown in FIG. 14.

The inlet conduit 15 includes a plurality of apertures 16 formed in the cylindrical wall near the distal end 15a. These apertures 16 constitute sparger means for distributing blood into the space 12 as a plurality of radial fine streams. Thus blood enters the space 12 through the inlet port 15 in a dispersed manner to ensure that blood calmly flows in the space 12. To this end, about 4 to 24 apertures each having a diameter of about 2 to about 5 mm, say about 3.5 mm, are arranged in the cylindrical wall of inlet conduit 15. For examples, two rows of 8 apertures (total 16 apertures) may be distributed.

A blood outlet port in the form of a conduit 17 is disposed in the bottom side 11d of casing 11, preferably at a location remote from the right side 11c where the inlet port 15 is disposed, that is, near the left side 11e. The outlet conduit 17 is integrally sealed between sheets 11a and 11b. The outlet conduit 17 extends vertically into the space 12 and has an inner end flush with the bottom of space 12. The outlet conduit 17 may be a plastic tube having an inner diameter of 10 mm and an outer diameter of 14 mm, for example.

The outlet conduit 17 is for discharging bubble-free blood from the space 12. An outer end of outlet conduit 17 is adapted to be connected to the circuit line C of the artificial heart-lung system S shown in FIG. 14.

The outlet port 17 is located relative to the inlet port 15 such that drained blood may follow a longer path from the inlet port 15, precisely sparging apertures 16 to the outlet port 17, increasing the chance or time for air bubbles in the blood to rise under the impetus of their own buoyancy.

Such a long path for blood can be obtained by arranging the respective elements in a preferred set of dimensions as given below. Provided that L is the lateral distance of the interior space 12 in the casing 11;

L1 is the lateral distance of the inlet conduit 15 protruding from the casing right side 11c to the distal end 15a;

L2 is the lateral distance from the centerline of the outlet port 17 to the left side 11e;

H is the maximum height or vertical distance of the interior space 12 in the casing 11; and H1 is the vertical distance from the centerline of the inlet port 15 to the bottom side 11d in FIG. 1, better results are achieved by determining these dimensions to the following ranges:

L1/L=0.1 to 0.5, especially 0.1 to 0.3,
L2/L=0.1 to 0.5, especially 0.1 to 0.3,
H1/H=0 (exclusive) to 0.8, especially 0.3 to 0.6,
L=5 to 30 cm, and
H=5 to 30 cm.

Figure 15:
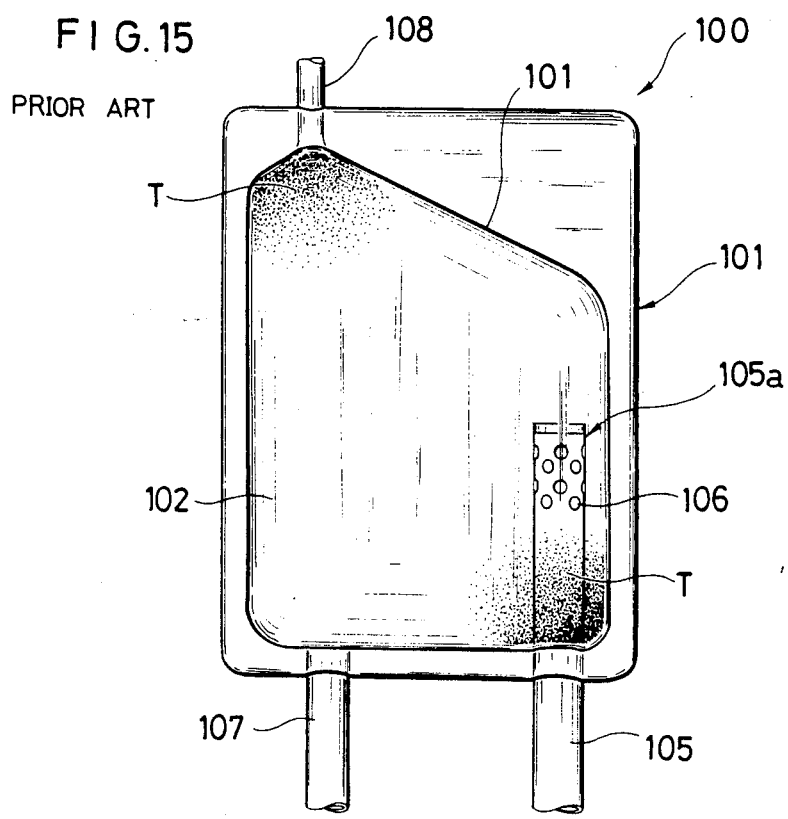
FIG. 15 is a front elevation of a prior art blood reservoir.

The blood reservoir 10 of the first embodiment is advantageous over the prior art blood reservoir shown in FIG. 15 in that the casing 11 can be of smaller dimensions. This is because the distal end 15a of the blood inlet conduit 15 can be set at a sufficient vertical distance to achieve the desired debubbling function without increasing the distance of the inlet conduit 15 extending into the space 12.

A vent port 18 is disposed in the top side 11f of the casing 11 which is the top wall of the blood storage space 12, preferably at the highest point of the space 12. The vent port 18 serves to discharge air resulting from debubbling of the drained blood in the space 12. The vent port 18 may be in the form of a vent line tube. The vent tube 18 is integrally sealed between sheets 11a and 11b (see FIG. 2). The location of the vent port 18 is not particularly limited as long as it is at the highest point of the space 12.

Preferably, the casing 11 includes a larger seal area near the top side 11f defining a slant ridge 11g for the space 12. The slant ridge 11g extends obliquely upward from the left side 11e at an appropriate lower position toward the right side 11c to the highest point where the vent port 18 is disposed. Then bubbles leaving the blood move upward along the ridge 11f toward the vent port 18. Preferably the ridge 11f is set at a slant angle of 30° to 60° with respect to the bottom side 11d or a horizontal direction.

FIGS. 3 through 13 show different examples of the blood reservoir according to the second embodiment of the present invention.

The blood reservoir 10 includes a flexible container casing 11 defining a space 12 for storing blood therein. The blood storage space 12 has a predetermined volume. In the illustrated embodiment, the casing 11 is of the structure consisting essentially of a pair of generally rectangular plastic front and rear sheets 11a and 11b. They are sealed together along the four sides. A seal S extends the entire perimeter of the sheets. The casing 11 has a generally rectangular contour in a vertical plane (as viewed in FIGS. 3, 5-8 and 13) defining a pair of vertically opposed top and bottom sides 11f and 11d and a pair of laterally opposed right and left sides 11c and 11e.

A blood inlet port in the form of a conduit 15 is disposed in the right side 11c of casing 11, preferably at approximately a midpoint thereof, for introducing blood into the space 12. A blood outlet port in the form of a conduit 17 is disposed in the casing bottom side 11d. A vent port 18 is disposed in the casing top side 11f. The inlet conduit 15 is not particularly limited as long as it is connectable at a rear end 15b to the extracorporeal circuit (not shown). Preferably, the inlet conduit 15 has a closed inner end and a plurality of sparger apertures 16 in the cylindrical wall near the inner end as in the first embodiment.

The above-mentioned arrangement is approximately the same as that of the first embodiment.

The difference of the second embodiment from the first embodiment is the provision of partition means in the form of a diaphragm 14 for separating the casing interior space into two compartments.

Figure 4:
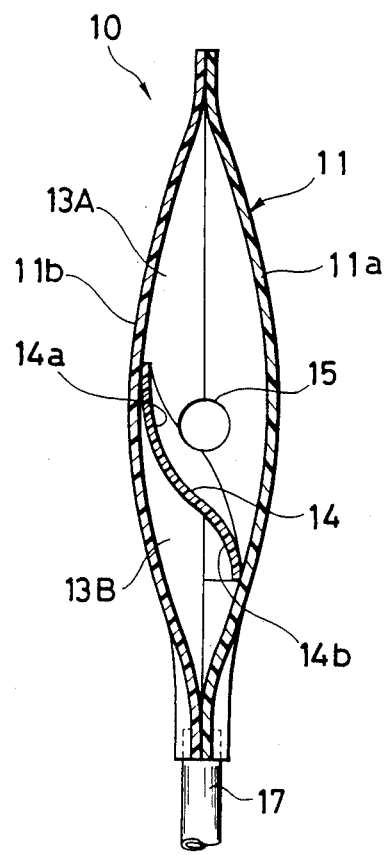
FIG. 4 is a cross section taken along lines IV—IV in FIG. 3.

As shown in FIG. 4, the diaphragm 14 is extended between the casing front and rear sheets 11a and 11b to constitute the partition means in the casing 11. The diaphragm 14 vertically separates the interior blood space 12 of the casing 11 into two blood compartments, a first or upper compartment 13A and a second or lower compartment 13B.

More particularly, the diaphragm 14 in the form of a flexible plastic sheet, preferably a flexible vinyl chloride resin sheet is attached at an upper side 14a to the casing front sheet 11a and at a lower side 14b to the casing rear sheet 11b to form seals S as by heat sealing or RF welding. The lateral sides of the diaphragm 14 are also sealed between the front and rear sheets 11a and 11b to form parts of the perimeter seal as seen from FIG. 3, for example.

The diaphragm 14 not only divides the interior blood space 12 of the casing 11 into two blood compartments, but also isolates the inlet port 15 and the outlet port 17 from each other. The diaphragm 14 separates the space 12 into the upper compartment 13A in communication with the inlet port 15 and the lower compartment 13B in communication with the outlet port 17.

Figure 3:
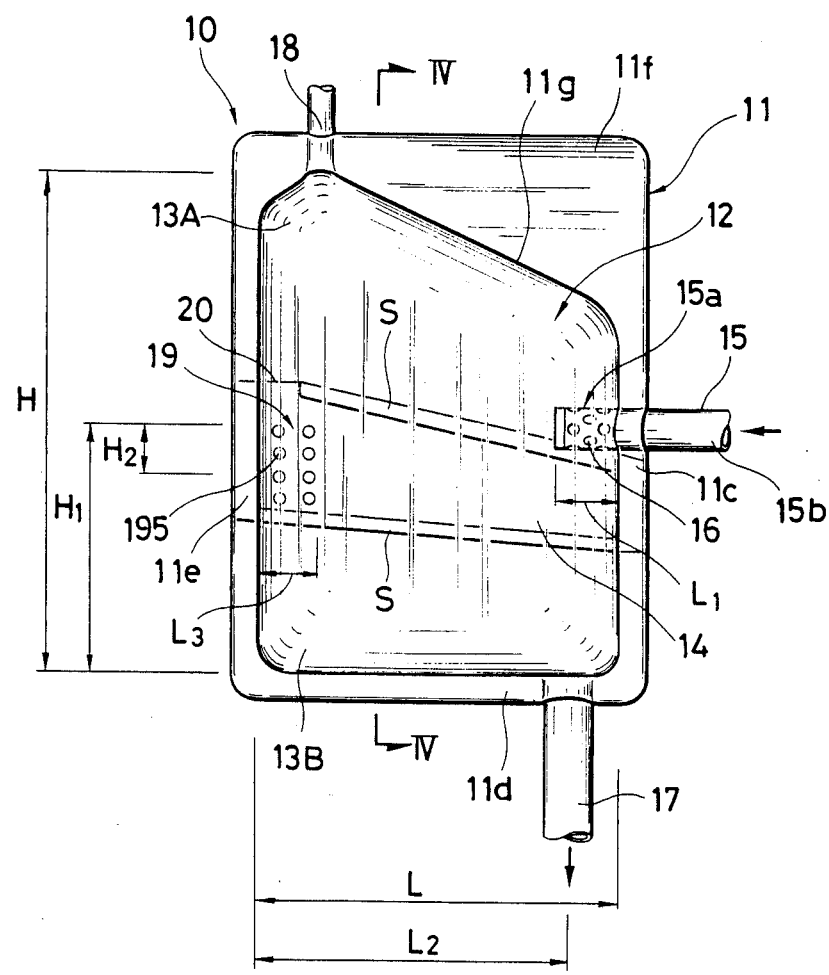
FIG. 3 is a front elevation of a blood reservoir according to a second embodiment of the invention.

As viewed in FIGS. 3 and 4, one side 14a of the diaphragm 14 secured to the rear sheet 11b is vertically above the other side 14b of the diaphragm 14 secured to the front sheet 11a. Thus the diaphragm 14 extends somewhat diagonally with respect to the opposed sheets 11a and 11b as seen from FIG. 4. The oblique arrangement of the diaphragm 14 minimizes deformation or distortion of the diaphragm due to variations of the blood volume in the casing while maintaining the necessary interior space volume.

Figure 5:
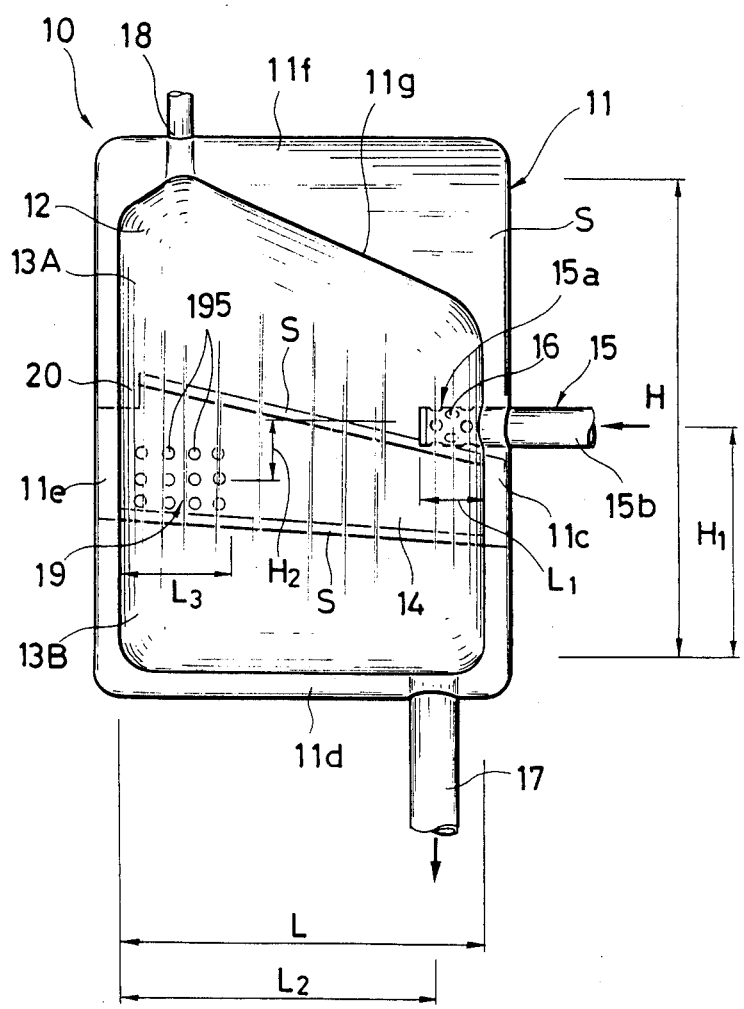
FIGS. 5 to 8 are front elevations of variant blood reservoirs according to the second embodiment of the invention.

In the examples shown in FIGS. 3 and 5, the diaphragm 14 has such a plane shape that the left side corresponding to the casing left side 11e is wider than the right side corresponding to the casing right side 11c where the inlet port 15 is disposed.

The partition means further includes blood communication means. The diaphragm 14 near the casing left side 11e is provided with communicating means 19 for blood communication between the upper and lower compartments 13A and 13B. The communicating means 19 is most often a plurality of apertures as will be described later.

The communicating means 19 is located for the following purposes. Since blood must pass the communicating means on its way through the casing 11 from the inlet port 15 to the outlet port 17, the blood travels a longer distance through the casing 11. The communicating means 19 limits the velocity at which blood flows from the upper compartment 13A to the lower compartment 13B, thereby moderating the streams of blood in both the compartments, eventually increasing the chance and time for bubbles to escape from the blood by floating upward by virtue of their own buoyancy.

To effectively achieve the purposes, the communicating means 19 is preferably located in a relatively lower portion of the diaphragm 14 adjacent or near the left side 11e remote from the inlet port 15.

Better results are obtained in this configuration when the outlet port 17 is provided in the bottom side 11d of casing 11 adjacent or near the right side 11c where the inlet port 15 is disposed.

Such a long path for blood and blood flow moderation can be achieved by arranging the respective elements in a preferred set of dimensions as given below. Provided that L is the lateral distance of the interior space 12 in the casing 11;

L1 is the lateral distance of the inlet conduit 15 protruding from the casing right side 11c to the distal end 15a;

L2 is the lateral distance from the centerline of the outlet port 17 to the left side 11e;

L3 is the lateral distance from the left side 11e to the farthest apertures of the communicating means 19;

H is the maximum height or vertical distance of the interior space 12 in the casing 11;

H1 is the vertical distance from the centerline of the inlet port 15 to the bottom side 11d; and H2 is the vertical distance between the centerline of the inlet port 15 to the vertical center of the communicating means 19 in FIG. 3, better results are achieved by determining these dimensions to the following ranges:

L1/L=0.1 to 0.5, especially 0.1 to 0.3,
L2/L=0.5 to 1 (exclusive), especially 0.7 to 0.9,
L3/L=0.1 to 0.5, especially 0.1 to 0.2,
H1/H=0 (exclusive) to 0.8, especially 0.3 to 0.6,
H2/H=0 (exclusive) to 0.6, especially 0 (exclusive) to 0.3,
L=5 to 30 cm, and
H=5 to 30 cm.

Various examples of the communicating means 19 are described. The communicating means 19 is most often constructed from a plurality of apertures.

More particularly, in the example shown in FIG. 3, the communicating means 19 includes two rows of 4 vertically spaced-apart circular apertures 195 (eight apertures in total). In the example shown in FIG. 5, the communicating means 19 includes four rows of 3 vertically spaced-apart circular apertures 195 (twelve apertures in total). The examples shown in FIGS. 7 and 13 also use a similar arrangement of circular apertures like FIGS. 3 and 5 as the communication means 19. Apertures are in rows in FIG. 3, 5, and 7 while they are in a zigzag arrangement in FIG. 13.

Figure 6:
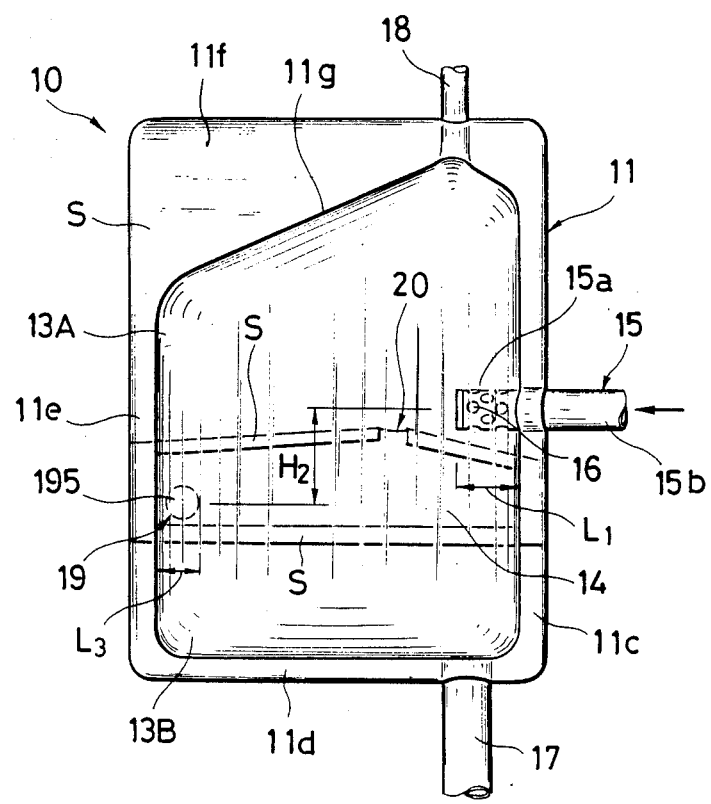

In the example shown in FIG. 6, the communicating means 19 includes only one relatively large circular aperture 195.

Figure 8:
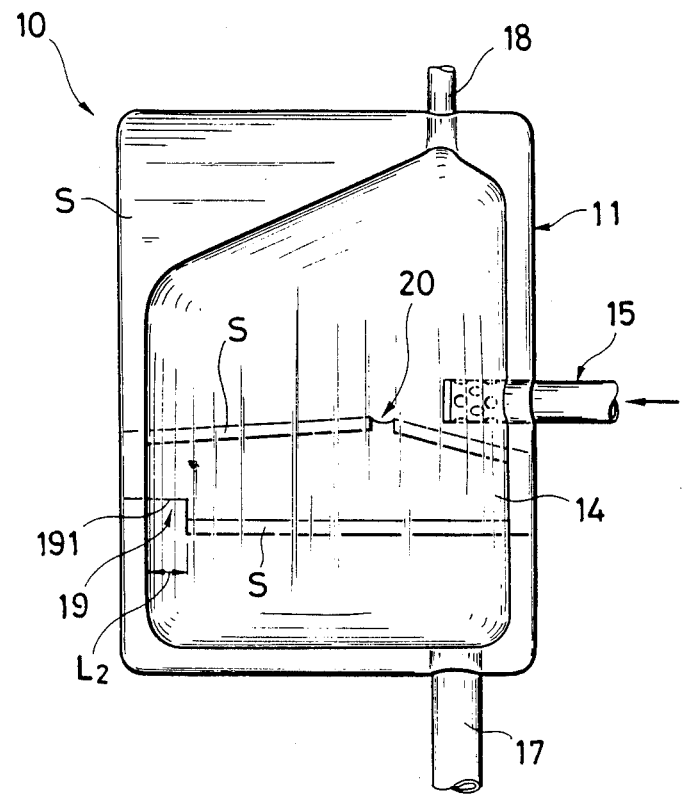

In the example shown in FIG. 8, the communicating means 19 is a generally rectangular slit 191 which is formed open between the diaphragm and the front sheet by leaving the relevant portions unsealed.

An arrangement of plural apertures 195 is preferred as the communicating means 19 in order to effectively prevent entry of bubbles into the lower compartment 13B from the upper compartment 13A. The communicating apertures 195 are preferably arranged at a diameter of about 1 to about 5 mm, a total number of 5 to 20, and a total area of about 100 to about 300 $mm^2$. Larger apertures 195 are rather less effective in preventing bubbles from entering the lower compartment 13B. A large pressure loss occurs across too smaller apertures, causing hemolysis.

Figure 13:
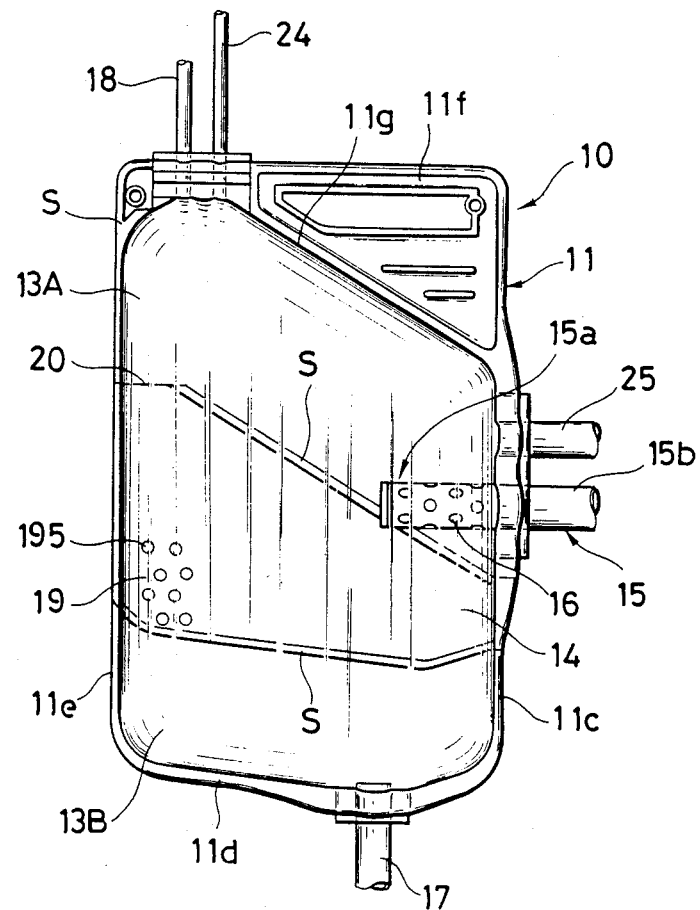
FIG. 13 is a front elevation of a further variant blood reservoir according to the second embodiment of the invention.

A plurality of apertures 195 are preferably distributed in a vertically elongated rectangular region having a larger vertical distance than a lateral distance as shown in FIGS. 3 and 13 rather than a laterally elongated rectangular region having a larger lateral distance than a vertical distance. This distribution allows setting of a reduced value of L3/L which is more effective in preventing bubbles from entering the lower compartment 13B.

For the communicating means 19, a desired number of apertures with a desired size may be formed by any conventional mechanical processing techniques as by punching out the diaphragm sheet.

The partition means further includes an intermediate vent port 20. More particularly, the intermediate vent port 20 is formed in the diaphragm 14 or between the diaphragm 14 and the rear sheet 11b.

In the example shown in FIG. 3, the diaphragm 14 is in the form of a plastic sheet having a wider left side and a narrower right side corresponding to the inlet port 15. The upper side of the plastic sheet diaphragm 14 is slanted such that the upper end of plastic sheet diaphragm 14 on the left side is at the vertically highest point. The diaphragm sheet 14 near the left side upper end is left unsealed to the rear sheet 11b to form a slit opening which constitutes the intermediate vent port 20.

The intermediate vent port 20 is provided for the purposes of allowing air to escape from the lower compartment upon priming and for allowing the air bubbles isolating from the blood in the lower compartment 13B to rise into the upper compartment 13A whereby the air bubbles will eventually escape to the exterior of the reservoir 10 through the vent port 18.

For these purposes, the intermediate vent port 20 is located at the vertically highest point of the diaphragm 14. The upper side of the diaphragm 14 along which it is sealed to the rear sheet 11b is slanted toward the intermediate vent port 20 at a sufficient angle to allow the air bubbles isolating from the blood in the lower compartment 13B to travel along the upper side toward the intermediate vent port 20. Preferably the diaphragm upper side is at an angle of 30° to 60° with respect to a horizontal direction.

Figure 9:
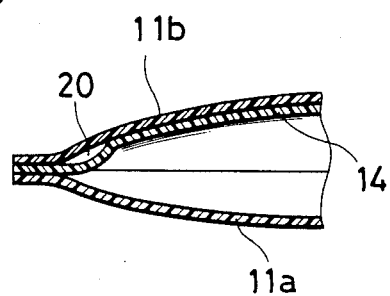
FIGS. 9 and 10 are horizontal cross sections of a portion of the casing of FIG. 5 surrounding an intermediate vent port, showing the operation thereof.
Figure 10:
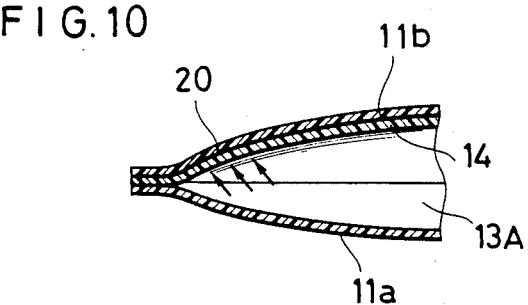

It is preferred that the intermediate vent port 20 takes the form of a slit formed as an unsealed area between the diaphragm 14 and the casing rear sheet 11b as shown in FIG. 3. The operation of the intermediate vent port 20 in the form of a slit is best shown in FIGS. 9 and 10. When some pressure is applied to the second or lower compartment 13B upon priming for the purpose of discharging air in the casing, the slit 20 is opened as shown in FIG. 9 allowing air to pass therethrough from the second or lower compartment 13B to the first or upper compartment 13A. During service for blood circulation, the pressure in the first or upper compartment 13A on the upstream side forces the diaphragm section against the rear sheet 11b to close the slit 20 as shown in FIG. 10, preventing blood communication therethrough. During service, air bubbles isolating from the blood in the lower compartment 13B gradually collect near the highest point or intermediate vent port 20. When such collecting bubbles exceed a certain volume, they act to open the slit 20 to escape from the lower compartment 13B to the upper compartment 13A. The air bubbles eventually go out of the reservoir through the vent port 18.

In the example of FIG. 5, the intermediate vent port 20 is in the form of a modified slit which is formed by further cutting out a rectangular portion surrounding the slit shown in FIG. 3. The upper side seal S is slanted toward the highest point or intermediate vent port 20.

Figure 7:
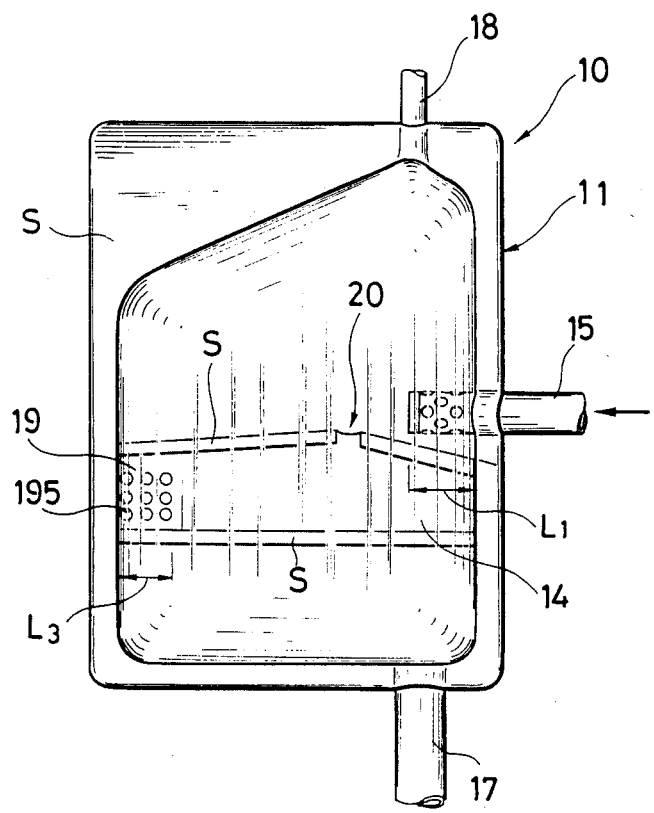

In the examples of FIGS. 6, 7, and 8, the diaphragm 14 is in the form of a plastic sheet whose vertical width is largest at a middle. The upper side of the diaphragm sheet at the highest middle point is left unsealed to the rear sheet 11b to form a slit or intermediate vent port 20. A slit-forming portion of the upper side of the diaphragm sheet 14 is cut out in arch form in the illustrated example. The upper side seal segments S are slanted toward the middle highest point or intermediate vent port 20 from the opposite sides.

The intermediate vent port 20 may be a slit or small opening in the diaphragm sheet 14 near its highest point.

It is seen that the vent port 18 at the top is located farthest from the inlet port 15 in the examples of FIGS. 3, 5, and 13, but on the same side as the inlet port 15 in the examples of FIGS. 6, 7, and 8. The location of the vent port 18 is not particularly limited as long as it is at the top of space 12. The blood storage space 12 preferably has an upper ridge 11g slanted toward the vent port 18 for allowing air bubbles to rise therealong. The slant ridge 11g preferably extends over at least one half of the lateral distance of the casing space (L). Such a requirement can be met independent of whether the vent port 18 at the top is located on the left or right side.

FIG. 13 shows a modified blood reservoir 10. A cardiotomy line inlet conduit 25 is connected to the casing 11 on the right side 11c above the blood inlet conduit 15. A medication conduit 24 is connected to the casing 11 on the top side 11f near the vent port 18.

The preferred embodiments of the present invention have been described. Many modifications and variations may be added to the first embodiment as long as a blood inlet port is on at least one of the lateral sides of the container casing and a blood outlet port is on the bottom side of the casing.

Also, many modifications and variations may be added to the second embodiment as long as the casing space is divided by partition means into two compartments, a blood inlet port and a vent port are connected to one of the compartments, and a blood outlet port is connected to the other of the compartments.

Although a flexible blood reservoir has been described in the embodiments, the present invention may be applicable to a non-flexible blood reservoir if desired. In such a case, many modifications and variations are made on the location of the blood inlet and outlet ports and the vent port and the structure of the partition means.

EXAMPLE

Examples of the present invention are given below by way of illustration and not by way of limitation.

Example 1

A blood reservoir of the two-compartment configuration shown in FIG. 5 was prepared using a pair of flexible vinyl chloride resin sheets. The reservoir had an overall interior volume of 1000 ml and a maximum blood circulating flow rate of 6 liter/min.

The inlet and outlet ports 15 and 17 were formed from flexible vinyl chloride resin tubes having an inner diameter of 10 mm. The inlet tube 15 laterally protruded 40 mm into the first compartment 13A from the right side 11c of the casing (L1=40 mm). The wall of inlet tube 15 near the inner end 15a was provided with sixteen sparging apertures 16 having a diameter of 3 mm in equally spaced-apart relation. The outlet tube 17 was connected to the bottom side 11d of the casing near the right side 11c.

The diaphragm 14 was a flexible vinyl chloride resin sheet having a vertical distance of 50 mm at the left side and 40 mm at the right side. The diaphragm sheet 14 near the left side was provided with twelve apertures 195 having a diameter of 5 mm.

The vent port 18 in the form of a flexible vinyl chloride resin tube and the slant ridge 11g of the space were as shown in FIG. 5.

The dimensions shown in FIG. 5 had the following values.
L=160 mm
L1=40 mm
L2=110 mm
L3=40 mm
H=230 mm
H1=110 mm
H2=35 mm

Example 2

This is a comparative example.

A blood reservoir of the configuration shown in FIG. 15 was prepared using a pair of flexible vinyl chloride resin sheets. The reservoir defined a single space 102 having a volume of 1000 ml and a maximum blood circulating flow rate of 6 liter/min.

The inlet and outlet ports 105 and 107 were formed from flexible vinyl chloride resin tubes having an inner diameter of 10 mm. The inlet tube 105 vertically protruded 110 mm into the space 102 from the bottom side of the casing. The wall of inlet tube 105 near the inner end 105a was provided with sixteen sparging apertures 106 having a diameter of 3 mm in symmetric relation. The outlet tube 107 was connected to the bottom side of the casing in parallel to the inlet tube 105.

The vent port 108 and the slant ridge of the space were approximately the same as in Example 1.

Example 3

A blood reservoir of the configuration shown in FIG. 1 was prepared. The materials and size of respective elements were substantially the same as in Example 1.

The dimensions shown in FIG. 1 had the following values.

L = 160 mm
L1 = 50 mm
H = 230 mm
H1 = 110 mm

Experiment 1: Blood stagnation in blood reservoir

Each of the blood reservoirs of Examples 1 to 3 was connected to an experimental circuit through which water was circulated at a flow rate of 4 liter/min. Black ink was introduced into the circuit line through a Luer port connector in the line upstream of the reservoir. Residence of black ink in the reservoir was observed.

In the reservoir of Example 2, black ink stagnation was observed in the shaded regions T in FIG. 15. Little or no stagnation was observed in the reservoirs of Examples 1 and 2.

Experiment 2: Debubbling

Each of the blood reservoirs of Examples 1 to 3 was connected to an experimental circuit through which bovine blood was circulated at a flow rate of 4 liter/min. Air was introduced into the circuit line at a flow rate of 100 ml/min. through a Luer port connector in the line upstream of the reservoir.

A ultrasonic bubble detector (Hatteland Bd100 system) was connected to the outlet port (17 or 107) of the blood reservoir to measure the size and number of air bubbles coming out of the outlet port.

The results are shown in Table 1.

TABLE 1

| Bubble size (μm) | Number of bubbles | | |
|---|---|---|---|
| | Example 1 | Example 2* | Example 3 |
| 10–20 | 75 | 140 | 112 |
| 21–30 | 15 | 44 | 27 |
| 31–40 | 1 | 19 | 4 |
| 41–50 | 0 | 6 | 2 |
| 51–60 | 0 | 1 | 0 |
| 61–70 | 0 | 0 | 0 |

*outside the scope of the invention

As seen from Table 1, the blood reservoirs of the present invention exhibit significantly improved debubbling function over the prior art reservoir. The prior art blood reservoir of Example 2 should undesirably be increased in volume to increase its debubbling performance. The blood reservoirs of the present invention achieve sufficient debubbling in a proper volume, that is, without increasing the volume.

Examples 4 and 5

These examples are to demonstrate the debubbling effect of means 19 in the diaphragm 14 for communication between two compartments.

Blood reservoirs of the configurations shown in FIGS. 7 and 8 were prepared. The materials and size of respective elements were substantially the same as in Example 1. The shape and size of the communicating means 19 are shown below.

In the reservoir of Example 4 shown in FIG. 7, the communicating means 19 was constructed by arranging ten apertures 195 having a diameter of 6 mm in a zigzag fashion (somewhat different from the figure). The apertures were equally spaced 10 mm.

In the reservoir of Example 5 shown in FIG. 8, the communicating means 19 was constructed by forming a rectangular slit 191 of 15 mm by 30 mm at the lower side of the diaphragm sheet adjacent the left side.

Each of the blood reservoirs of Examples 4 and 5 was connected to an experimental circuit which was primed with 1000 ml of bovine blood. Bovine blood was circulated through the circuit at a flow rate of 4 liter/min. Air was introduced into the circuit line at a flow rate of 50 ml/10 sec. (300 ml/min.) through a Luer port connector in the line upstream of the reservoir.

A ultrasonic bubble detector (Hatteland Bd100 system) was connected to the outlet port 17 of the blood reservoir to measure the size and number of air bubbles coming out of the outlet port.

The results are shown in Table 2.

TABLE 2

| Bubble size (μm) | Number of bubbles | |
|---|---|---|
| | Example 4 | Example 5 |
| 11–20 | 60 | 80 |
| 21–30 | 13 | 31 |
| 31–40 | 2 | 5 |
| 41–50 | 0 | 1 |

As seen from Table 2, an arrangement of apertures is more effective in debubbling than a slit as the means 19 for communication between two compartments.

Examples 6 and 7

These examples are to demonstrate the debubbling effect of an arrangement of apertures in the diaphragm 14 as the means 19 for communication between two compartments.

Blood reservoirs of the configuration shown in FIG. 5 were prepared. The materials and size of respective elements were substantially the same as in Example 1. The communicating means 19 used were an array of eight apertures 195 each having a diameter of 6 mm.

Figure 11:
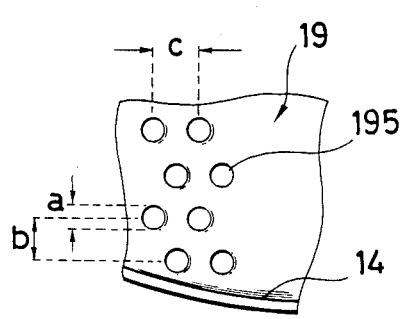
FIGS. 11 and 12 are partial elevational views showing communicating means in the form of a plurality of apertures, showing the distribution of apertures.

In the reservoir of Example 6, eight apertures are arranged in a vertically elongated region in a zigzag manner, more exactly in four lateral lines each containing two apertures as shown in FIG. 11.

Figure 12:
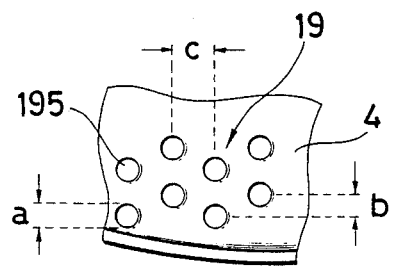

In the reservoir of Example 7, eight apertures are arranged in a laterally elongated region in a zigzag manner, more exactly in four vertical rows each containing two apertures as shown in FIG. 12.

Each of the blood reservoirs of Examples 6 and 7 was connected to an experimental circuit which was primed with 1000 ml of bovine blood. Bovine blood was circulated through the circuit at a flow rate of 4 liter/min. Air was introduced into the circuit line at a flow rate of 100 ml/10 sec. (600 ml/min.) through a Luer port connector in the line upstream of the reservoir.

A ultrasonic bubble detector (Hatteland Bd100 system) was connected to the outlet port 17 of the blood reservoir to measure the size and number of air bubbles coming out of the outlet port.

The results are shown in Table 3.

TABLE 3

| Bubble size (μm) | Number of bubbles | |
|---|---|---|
| | Example 6 | Example 7 |
| 11–20 | 195 | 224 |
| 21–30 | 47 | 63 |
| 31–40 | 7 | 10 |
| 41–50 | 0 | 0 |

As seen from Table 3, an arrangement of apertures in a vertically elongated region as shown in FIG. 11 is more effective in debubbling.

A novel blood reservoir having an improved debubbling function and free of local blood stagnation has been described.

Although some preferred embodiments have been described, many modifications and variations may be made thereto in the light of the above teachings. It is therefore to be understood that within the scope of the appended claims, the invention may be practiced otherwise than as specifically described.

I claim:

1. A blood reservoir, comprising:
   a container casing defining a space for accommodating blood, said casing having a generally rectangular contour in a vertical plane defining a pair of upper and lower sides each of a length L and a pair of laterally opposed sides each of a height H when said casing assumes a vertically upright attitude,
   an inlet port disposed in at least one of the laterally opposed sides of said casing for introducing blood into said space, said inlet port extending into said case horizontally a distance of L1 and having a center axis spaced apart from the lower side of said casing by a distance of H1,
   an outlet port disposed in the lower side of said casing for discharging blood from said space, a center axis of said outlet port being spaced apart from the other one of said laterally opposed sides by a distance of L2, and
   a vent port disposed in the upper side of said casing in fluid communication with said space;
   wherein said inlet port comprises a cylindrical conduit extending from the exterior into said space through the one lateral side of said casing, and the portion of said conduit in the casing includes a closed distal end and a plurality of apertures formed in an adjoining cylindrical wall thereof for introducing blood into said space in a dispersed manner, and the following dimensional relationships are established:
   L1/L is in the range of about 0.1 to 0.3;
   L2/L is in the range of about 0.1 to 0.3; and
   H1/H is in the range of about 0.3 to 0.6.

2. A blood reservoir according to claim 1, wherein said plurality of apertures are formed in substantially the entire cylindrical wall of said conduit forming the inlet port within said space.

3. A blood reservoir according to claim 1 wherein said container casing is flexible.

4. A blood reservoir according to claim 1 wherein
   said inlet port is disposed in one lateral side of said casing,
   said outlet port is disposed in the lower side of said casing near the other lateral side.

5. A blood reservoir according to claim 1 wherein the upper side of said container casing includes a bevel portion extending toward said vent port.

6. A blood reservoir according to claim 1 wherein said container casing includes a pair of generally rectangular sheets which are sealed together along the four sides with said inlet port, said outlet port and said vent port interposed therebetween.

7. A blood reservoir comprising
   a container casing defining a space, said casing having a generally rectangular contour in a vertical plane defining a pair of upper and lower sides and a pair of laterally opposed sides, provided that said casing assumes a vertically upright attitude,
   partition means for separating the space into first and second compartments for accommodating blood, but allowing partial fluid communication between the first and second compartments,
   an inlet port in a lateral side of said casing in communication with said first compartment,
   an outlet port disposed in the lower side of said casing in communication with said second compartment, and
   a vent port disposed in the upper side of said casing in communication with said first compartment.

8. A blood reservoir according to claim 7 wherein said inlet port comprises a cylindrical conduit extending from the exterior into said space.

9. A blood reservoir according to claim 8 wherein the portion of said conduit in the casing includes a closed distal end and a plurality of apertures formed in an adjoining cylindrical wall thereof for introducing blood into said space therethrough in a dispersed manner.

10. A blood reservoir according to claim 9, wherein said plurality of apertures are formed in substantially the entire cylindrical wall of said conduit forming the inlet port within said space.

11. A blood reservoir according to claim 7 wherein said container casing is flexible.

12. A blood reservoir according to claim 7 wherein said partition means includes a flexible diaphragm separating the space into the first and second compartments and means formed in said diaphragm for fluid communication between said first and second compartments.

13. A blood reservoir according to claim 12 wherein said first compartment is vertically above said second compartment and said inlet port is disposed in one of the laterally opposed sides of said casing.

14. A blood reservoir according to claim 13 wherein said communicating means in said diaphragm is near the other lateral side of said casing remote from the one lateral side where said inlet port is disposed.

15. A blood reservoir according to claim 13 wherein said outlet port is disposed in the lower side of said casing near the one lateral side where said inlet port is disposed.

16. A blood reservoir according to claim 12 wherein said communicating means includes a plurality of apertures formed in said diaphragm.

17. A blood reservoir according to claim 16 wherein said apertures are distributed over a region on said diaphragm near the other lateral side of said casing remote from the one lateral side where said inlet port is disposed, said region having a longer vertical distance than a lateral distance.

18. A blood reservoir according to claim 12 which further comprises an intermediate vent port disposed in said diaphragm or between said diaphragm and said casing near the vertically upper portion of said diaphragm for air communication from said second compartment to said vent port.

19. A blood reservoir according to claim 18 wherein said intermediate vent port is in the form of a slit.

20. A blood reservoir according to claim 7 wherein the upper side of said container casing includes a bevel portion for said first compartment extending toward said vent port.

21. A blood reservoir according to claim 7 wherein said container casing includes a pair of generally rectangular sheets which are sealed together along the four sides with said inlet port, said outlet port, said vent port, and said partition means interposed therebetween.

22. A blood reservoir according to claim 21 wherein said partition means is a flexible diaphragm having opposed sides sealingly attached to said pair of sheets for separating the space into the first and second compartments, and one side of said diaphragm attached to one sheet is vertically above the other side of said diaphragm attached to the other sheet.

* * * * *

UNITED STATES PATENT AND TRADEMARK OFFICE
CERTIFICATE OF CORRECTION

PATENT NO. : 4,976,708

DATED : December 11, 1990

INVENTOR(S) : Hiroaki OSHIYAMA

It is certified that error appears in the above-identified patent and that said Letters Patent is hereby corrected as shown below:

In the title page:

Section 56 "References Cited"

change 69-67962 to --59-67962--

In Column 11, line 41, change "2" to --3--.

Signed and Sealed this

Thirty-first Day of May, 1994

*Attest:*

BRUCE LEHMAN

*Attesting Officer*   *Commissioner of Patents and Trademarks*